United States Patent

Ebel et al.

Patent Number: 5,292,894
Date of Patent: Mar. 8, 1994

[54] PREPARATION OF BENZO[B]THIOPHENES

[75] Inventors: Klaus Ebel, Mutterstadt; Juergen Schroeder, Viernheim, both of Fed. Rep. of Germany

[73] Assignee: BASF Aktiengesellschaft, Ludwigshafen, Fed. Rep. of Germany

[21] Appl. No.: 18,499

[22] Filed: Feb. 17, 1993

[30] Foreign Application Priority Data

Feb. 19, 1992 [DE] Fed. Rep. of Germany ....... 4204969

[51] Int. Cl.$^5$ ............................................. C07D 333/54
[52] U.S. Cl. ..................................... 549/43; 549/44; 549/48; 549/49; 549/51; 549/57; 549/58; 568/433
[58] Field of Search ............... 549/49, 51, 57, 58, 549/55, 43, 44, 48

[56] References Cited

U.S. PATENT DOCUMENTS

5,169,961 12/1992 Dickman et al. ...................... 549/52

OTHER PUBLICATIONS

A. R. Katritzky et al Adv. Heterocyclic Chemistry, 11, 206–239 (1970).
B. D. Tilak, Proc. Indian Academy of Sciences: 32A, 390–395 (1950).
Collin et al Ullmann's Encyclopedia D. Tech Chem. vol. 23, pp. 217–225, 4th Edition (1982).
O. DeLucchi, et al. *J. Chem Soc, Chem: Commun.*, pp. 513–514 (1984).
T. Greene, "Protective Groups in Organic Synthesis", pp. 114–121 John Wiley & Sons, New York (1981).

*Primary Examiner*—Richard L. Raymond
*Attorney, Agent, or Firm*—Keil & Weinkauf

[57] ABSTRACT

A process for the preparation of benzo[b]thiophenes of the general formula I

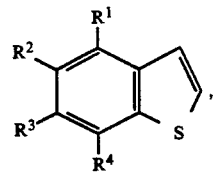

in which $R^1$, $R^2$, $R^3$, $R^4$ independently denote hydrogen, $C_1$–$C_4$ alkyl, $C_1$–$C_4$ alkoxy, $C_1$–$C_4$ haloalkyl, nitro, cyano, halo, $C_1$–$C_4$ alkylcarbonyl, benzoyl, $C_1$–$C_4$ alkylcarbonylamino, benzoylamino, N-($C_1$–$C_4$ alkyl)-phenylamino, $C_1$–$C_4$ alkoxycarbonyl, $C_1$–$C_4$ alkylsulfonyl, phenylsulfonyl, aminosulfonyl, aminocarbonyl, $C_1$–$C_4$ phenylalkyl and nitrobenzyl or $R^1+R^2$ or $R^2+R^3$ or $R^3+R^4$ denote a butadienediyl chain optionally substituted by $R^1$ to $R^4$, in which a) thiophenols of the general formula II

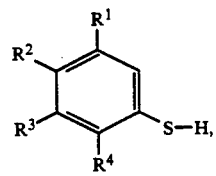

in which the substituents $R^1$ to $R^4$ have the aforementioned meanings, are reacted with chloroacetaldehyde at a temperature ranging from 0° to 150° C. and b) the resulting (arylthio)acetaldehydes of the general formula III

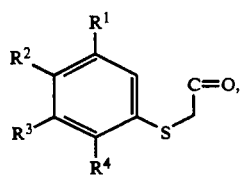

in which the substituents $R^1$ to $R^4$ have the aforementioned meanings, are cyclized by passing them into polyphosphoric acid or a mixture of phosphoric acid and phosphorus pentoxide at a temperature ranging from 100° to 300° C., and a pressure ranging from 0.001 to 1 bar.

4 Claims, No Drawings

PREPARATION OF BENZO[B]THIOPHENES

This invention relates to a novel process for the preparation of benzo[b]thiophenes by the reaction of thiophenols with chloroacetaldehyde to form the (arylthio)acetaldehydes and the subsequent cyclization thereof.

*Adv. Heterocycl. Chem.* 11 pp. 206 to 239 (1970) discloses various processes for the preparation of benzo[b]thiophenes. These processes are unsuitable for large scale manufacture on account of their expensive starting materials or their poor yields.

*Proc. Indian Acad. Sci.* 32A pp. 390 to 395 (1950) discloses a two-stage benzo[b]thiophene synthesis. In the first stage thiophenols are reacted with bromoacetaldehyde acetals in the presence of equimolar amounts of sodium alcoholate to form (arylthio)acetaldehyde acetals. The (arylthio)acetaldehyde acetals are cyclized in polyphosphoric acid at a temperature ranging from 160° to 180° C. The benzo[b]thiophenes can be distilled off continuously. The starting materials are too expensive for large scale manufacture and, besides, equimolar amounts of salt are obtained.

Consequently, the synthesis of benzo[b]thiophene, as opposed to its extraction from coal tar, has hitherto achieved no significance (*Ullmanns Enzyklopädie der technischen Chemie*, 4th Edition, Vol. 23, pp. 217 to 225).

It is thus an object of the present invention to overcome the aforementioned disadvantages.

Accordingly, we have found a novel and improved process for the preparation of benzo[b]thiophenes of the general formula I

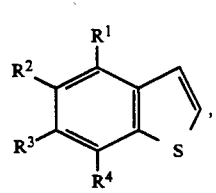
(I)

in which $R^1$, $R^2$, $R^3$, $R^4$ independently denote hydrogen, $C_1$–$C_4$ alkyl, $C_1$–$C_4$ alkoxy, $C_1$–$C_4$ haloalkyl, nitro, cyano, halo, $C_1$–$C_4$ alkylcarbonyl, benzoyl, $C_1$–$C_4$ alkylcarbonylamino, benzoylamino,N-($C_1$–$C_4$ alkyl)-phenylamino, $C_1$–$C_4$ alkoxycarbonyl, $C_1$–$C_4$ alkylsulfonyl, phenylsulfonyl, aminosulfonyl, aminocarbonyl, $C_1$–$C_4$ phenylalkyl and nitrobenzyl or $R^1+R^2$ or $R^2+R^3$ or $R^3+R^4$ denote a butadienediyl chain optionally substituted by $R^1$ to $R^4$, wherein a) thiophenols of the general formula II

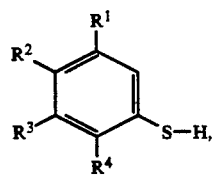
(II)

in which the substituents $R^1$ to $R^4$ have the aforementioned meanings, are reacted with chloroacetaldehyde at a temperature ranging from 0° to 150° C. and b) the resulting (arylthio)acetaldehydes of the general formula III

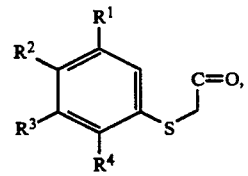
(III)

in which the substituents $R^1$ to $R^4$ have the aforementioned meanings, are cyclized by passing them into polyphosphoric acid or a mixture of phosphoric acid and phosphorus pentoxide at a temperature ranging from 100° to 300° C. and a pressure ranging from 0.001 to 1 bar.

The process of the invention may be carried out as follows:

a) In the first stage the thiophenols II can be reacted with chloroacetaldehyde, preferably aqueous chloroacetaldehyde, at a temperature ranging from 0° to 150° C., preferably at from 40° to 100° C., and preferably water and hydrogen chloride can be distilled off azeotropically using a suitable solvent such as a $C_4$–$C_{30}$ alkane or $C_4$–$C_{30}$ cycloalkane, e.g., cyclohexane, or a halogenated hydrocarbon, e.g., chloroform.

The thiophenols II and chloroacetaldehyde can be used in a molar ratio of from 0.1:1 to 5:1 and preferably from 0.5:1 to 1.5:1 and more preferably from 0.8:1 to 1.2:1.

b) In the second stage, the crude (arylthio)acetaldehyde III obtained in the first stage, preferably in the solvent used in the first stage, is passed, at a pressure of from 0.001 to 1 bar and preferably from 0.002 to 0.5 bar and more preferably from 0.005 to 0.2 bar, into polyphosphoric acid preheated to a temperature of from 100° to 300° C., preferably from 150° to 250° C. and more preferably from 150° to 200° C. or into a mixture of phosphoric acid and phosphorus pentoxide. The pressure and temperature conditions are advantageously set such that the benzo[b]thiophene I distils off continuously.

Compared with prior art processes, the process of the invention produces the benzo[b]thiophenes I in good yields and in a simpler and more economical manner, although the (arylthio)acetaldehydes III are unstable (*J. Chem. Soc., Chem. Commun.* pp. 513 to 514 (1984)).

The substituents $R^1$, $R^2$, $R^3$, $R^4$ in the compounds of the formulae I, II and III have the following meanings:

$R^1$, $R^2$, $R^3$, $R^4$ independently denote hydrogen, $C_1$–$C_4$ alkyl such as methyl, ethyl, n-propyl, isopropyl, n-butyl, isobutyl, sec-butyl and tert.-butyl, preferably methyl, ethyl, n-propyl and isopropyl, more preferably methyl and ethyl, $C_1$–$C_4$ alkoxy, such as methoxy, ethoxy, n-propoxy, isopropoxy, n-butoxy, isobutoxy, sec-butoxy and tert-butoxy, preferably methoxy, ethoxy, n-propoxy and isopropoxy, more preferably methoxy and ethoxy, halo($C_1$–$C_4$ alkyl), preferably fluoro-, chloro- and/or bromo-($C_1$–$C_4$ alkyl) such as fluoromethyl, difluoromethyl, trifluoromethyl, chloromethyl, dichloromethyl, trichloromethyl, bromomethyl, dibromomethyl and tribromomethyl, nitro, cyano, halogen such as fluorine, chlorine, bromine and iodine, preferably fluorine, chlorine and bromine, more preferably chlorine and bromine, $C_1$–$C_4$ alkylcarbonyl such as methylcarbonyl, ethylcarbonyl, n-propylcarbonyl, isopropylcarbonyl, n-butylcarbonyl, isobutylcarbonyl, sec-butylcarbonyl and tert-butylcarbonyl, preferably methylcarbonyl, ethylcarbonyl, n-propylcarbonyl and isopropylcarbonyl, more preferably methylcarbonyl and ethylcarbonyl, benzoyl, $C_1$–$C_4$ alkylcarbonylamino such as methylcarbonylamino, ethylcarbonylamino, n-propylcarbonylamino, isopropylcarbonylamino, n-butylcarbonylamino, isobutylcarbonylamino, sec-butylcarbonylamino, and tert-butylcarbonylamino, preferably methylcarbonylamino, ethylcarbonylamino, n-propylcarbonylamino and isopropylcarbonylamino, more preferably methylcarbonylamino and ethylcarbonylamino, benzoylamino, N-($C_1$–$C_4$ alkyl)phenylamino such as methylphenylamino, ethylphenylamino, n-propylphenylamino, isopropylphenylamino, n-butylphenylamino, isobutylphenylamino, sec-butylphenylamino and tert-butylphenylamino, preferably methylphenylamino, ethylphenylamino, n-propylphenylamino and isopropylphenylamino, more preferably methylphenylamino and ethylphenylamino, $C_1$–$C_4$ alkoxycarbonyl such as methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl, preferably methoxycarbonyl, ethoxycarbonyl, n-propoxycarbonyl and isopropoxycarbonyl, more preferably methoxycarbonyl and ethoxycarbonyl, $C_1$–$C_4$ alkylsulfonyl such as methylsulfonyl, ethylsulfonyl, n-propylsulfonyl, isopropylsulfonyl, n-butylsulfonyl, isobutylsulfonyl, sec-butylsulfonyl and tert-butylsulfonyl, preferably methylsulfonyl, ethylsulfonyl, n-propylsulfonyl and isopropylsulfonyl, more preferably methylsulfonyl and ethylsulfonyl, phenylsulfonyl, aminosulfonyl, aminocarbonyl, phenyl($C_1$–$C_4$ alkyl) such as benzyl, 1-phenethyl, and 2-phenethyl and nitrobenzyl or $R^1$+$R^2$ or $R^2$+$R^3$ or $R^3$+$R^4$ denote a butadienediyl chain optionally substituted by $R^1$ to $R^4$, as in 1-thionaphthol and 2-thionaphthol.

Benzo[b]thiophenes are valuable intermediates for the preparation of plant protectants and pharmaceuticals (*Ullmanns Enzyklopädie der technischen Chemie*, 4th Edition, Vol. 23, pp. 217 to 225).

EXAMPLES

Example 1

Stage 1:

In a four-necked flask having a capacity of 2 L and equipped with a stirrer, thermometer, drip funnel, and water trap, there are placed 220 g of thiophenol and 280 g of cyclohexane. At room temperature there are slowly added dropwise, with stirring, 314 g of a 50% strength aqueous chloroacetaldehyde solution. The water is then removed by azeotropic distillation. The crude solution (ca 45% strength) is used without purification in the second stage. The yield is 80%.

Stage 2:

In a four-necked flask having a capacity of 500 mL and equipped with a stirrer, thermometer, drip funnel, and distillation bridge, there are placed 100 g polyphosphoric acid. At 160° C. and 0.1 bar, the crude solution from the first stage is added dropwise. There are obtained 190 g of distillate having the following composition, as determined chromatographically and expressed as percentage area: 35% of thiophenol, 60% of benzo[b]thiophene and 2% of (phenylthio)acetaldehyde. The cyclohexane is condensed in a cold trap. The crude product is distilled. There are obtained 92 g (44%) of benzo[b]thiophene boiling at 115° C./40 mbar and having a purity of 98%.

Example 2

Stage 1:

Example 1 is repeated except that 248 g of 4-thiocresol are used. The crude solution (ca 50% strength) is used in the second stage without purification. The yield is 85%.

Stage 2:

Example 1 is repeated except that cyclization is carried out at 160° C./5 mbar. There are obtained 208 g of crude distillate having the following composition, as determined chromatographically and expressed as percentage area: 20% of 4-thiocresol, 63% of 5-methylbenzo[b]thiophene and 15% of 4-(methylphenylthio)acetaldehyde. The crude product is distilled to give 133 g (53%) of 5-methylbenzo[b]thiophene boiling at 102° C./32 mbar and having a purity of 98%.

We claim:

1. A process for the preparation of a benzo[b]thiophene of the general formula I below

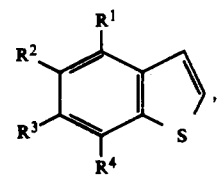

(I)

in which $R^1$, $R^2$, $R^3$, $R^4$ independently denote hydrogen, $C_1$–$C_4$ alkyl, $C_1$–$C_4$ alkoxy, $C_1$–$C_4$ haloalkyl, nitro, cyano, halo, $C_1$–$C_4$ alkylcarbonyl, benzoyl, $C_1$–$C_4$ alkylcarbonylamino, benzoylamino, N-($C_1$–$C_4$ alkyl)-phenylamino, $C_1$–$C_4$ alkoxycarbonyl, $C_1$–$C_4$ alkylsulfonyl, phenylsulfonyl, aminosulfonyl, aminocarbonyl, $C_1$–$C_4$ phenylalkyl and nitrobenzyl or $R^1$+$R^2$ or $R^2$+$R^3$ or $R^3$+$R^4$ denote a butadienediyl chain optionally substituted by $R^1$ to $R^4$, wherein a) a thiophenol of the general formula II

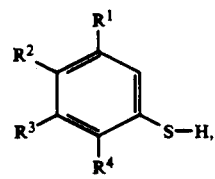

(II)

in which the substituents $R^1$ to $R^4$ have the aforementioned meanings, is reacted with chloroacetaldehyde at a temperature ranging from 0° to 150° C. and b) the resulting (arylthio)acetaldehyde of the general formula III

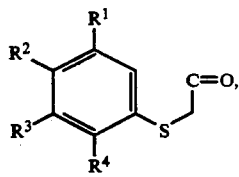

(III)

in which the substituents $R^1$ to $R^4$ have the aforementioned meanings, is cyclized by passing them into polyphosphoric acid or a mixture of phosphoric acid and phosphorus pentoxide at a temperature ranging from 100° to 300° C. and a pressure ranging from 0.001 to 1 bar.

2. A process for the preparation of benzo[b]thiophenes of the general formula I as claimed in claim 1, wherein water is distilled off azeotropically from the reaction mixture.

3. A process for the preparation of benzo[b]thiophenes of the general formula I as claimed in claim 1, wherein cyclization is carried out using polyphosphoric acid.

4. A process for the preparation of benzo[b]thiophenes of the general formula I as claimed in claim 1, wherein cyclization is carried out using a mixture of phosphoric acid and phosphorus pentoxide.

* * * * *